United States Patent [19]

Stokar

[11] Patent Number: 5,035,244
[45] Date of Patent: Jul. 30, 1991

[54] MOTION ARTIFACT MINIMIZATION

[75] Inventor: Saul Stokar, Raanana, Israel
[73] Assignee: Elscint Ltd., Haifa, Israel
[21] Appl. No.: 472,431
[22] Filed: Feb. 1, 1990

Related U.S. Application Data

[63] Continuation of Ser. No. 159,124, Feb. 23, 1988, abandoned.

[51] Int. Cl.$^5$ .............................................. A61B 5/055
[52] U.S. Cl. ............................... 128/653 A; 128/721; 324/309
[58] Field of Search .......................... 128/653 A, 721; 324/307, 309

[56] References Cited

U.S. PATENT DOCUMENTS

| | | |
|---|---|---|
| 4,564,017 | 1/1986 | Glover . |
| 4,567,893 | 2/1986 | Charles et al. . |
| 4,614,195 | 9/1986 | Bottomley et al. ................ 128/653 |
| 4,706,026 | 11/1987 | Pelc et al. ............................. 324/309 |
| 4,724,386 | 2/1988 | Haacke et al. ........................ 324/309 |
| 4,727,882 | 3/1988 | Schneider et al. .................. 128/653 |
| 4,730,620 | 3/1988 | Bailes ................................... 128/653 |
| 4,779,620 | 10/1988 | Zimmermann et al. ............. 128/653 |

OTHER PUBLICATIONS

"Respiratory Ordered Phase Encoding (ROPE): A Method for Reducing Motion Artifacts in MR Imaging", by D. R. Bailes et al., pp. 835-838, Journal of Computer Assisted Tomography, vol. 9, (4) Jul./Aug. 1985.

Reducing Motion Artifacts in Two-Dimensional Fourier Transform Imaging; E. Mark Haacke and John L. Patrick; Magnetic Resonance Imaging, vol. 4, pp. 359-376, 1986.

*Primary Examiner*—Ruth S. Smith
*Attorney, Agent, or Firm*—Sandler, Greenblum & Bernstein

[57] ABSTRACT

A method for reducing respiratory motion caused artifacts in magnetic resonance imaging. The respiration cycle amplitude of the patient is divided into a plurality of intervals. Each interval is assigned a preferred encoding pulse. If the preferred encoding pulse has been used the next sequential (higher or lower) unused phase encoding pulse of a valve that is ±50% of the originally preferred phase encoding pulse is used.

7 Claims, 1 Drawing Sheet

MOTION ARTIFACT MINIMIZATION

This application is a continuation of application Ser. No. 159,124, filed Feb. 23, 1988 now abandoned.

FIELD OF THE INVENTION

This invention is concerned with magnetic resonance methods and apparatus and more particularly, with methods and apparatus for reducing motion artifacts induced by respiratory motion of patients in magnetic resonance imaging (MRI).

BACKGROUND OF THE INVENTION

One of the major problems presently faced by the suppliers of MRI equipment is motion artifacts, particularly in the imaging of the upper thorax and the abdomen. A primary cause of the motion artifacts is motion due to the patient's breathing. Breathing introduces quasi-cyclical changes in the RF data signals received by the MRI system's receiver. The quasi-cyclic nature of the breathing causes a "foreign" frequency to be introduced into the image which multiplies the number of appearances of the lives of the image. Each appearance is slightly displaced from the other appearances. The artifact is known as "ghosting" and appears along the phase encoding axis, lowering the clarity of the image. The ghosts make it difficult to determine lesions in the image. As these quasi-cyclic changes result from non-linear motions along all three axes, to date no software post aquisition processing method has been discovered that is completely effective in correcting the resulting artifacts.

The prior art reveals numerous approaches and methods which have been tried in attempts to minimize the artifacts caused by the breathing of the subject during the MRI process. For example, various post acquisition data processing methods have been tried to reduce the artifacts. Post-processing methods are model dependant. This approach, however, in addition to the aforementioned problem of the three dimensional motion and model dependency inherently requires significantly more time per patient. Since "throughput" is a key requirement of any MRI system, scientists in the field are continually seeking faster alternatives to such time intensive prior art processes.

In the past, those skilled in the art attempted to minimize such motion artifacts by various breathing gating or triggering schemes. A serious drawback in the use of gating schemes, among other things, is that respiratory gating or triggering requires additional sophisticated and expensive equipment to generate gating signals and also requires appreciably longer data acquisition time periods with consequent reduced throughput.

More particularly, respiratory triggering comprises waiting with an encoding pulse train until the selected thoracic position occurs. This means that there is no exact repetition time TR, but rather the repetition is controlled by the breathing. In gating TR=C (a constant)—all portions of the breathing cycle outside of a "window" are rejected. Gating and triggering thus inherently limit the user, as TR is an important factor effecting image quality. Its control is usually left to the user as a tool in selecting the type of contrast desired. In gating, TR is a few seconds instead of the usual TR time of under a second, causing the gated study to last much longer than a non-gated study.

More recently, methods have been used which allow the user to fix TR, but couple the encoding pulse's amplitude to the thoracic position instead of linearly increasing the amplitude at each pulse repetion as is the usual procedure. See for example, the technical note entitled "Respiratorily Ordered Phase Encoding (ROPE): A Method for Reducing Motion Artifacts in MR Imaging" by D. R. Bailes et al, pp 835-838, Journal of Computer Assisted Tomography, vol. 9,(4) July/August 1985; U.S. Pat. Nos. 4,564,017 and 4,567,893.

A popular method makes the encoding amplitude a monotonic function of the thoraxic position. Thus, in theory after reordering the encoding pulse amplitude, most of the effects of the breathing frequency are eliminated. In fact, what this does is change the quasi-cyclic nature of the breathing into a quasi-linear function or a slowly changing function.

Making the encoding pulse amplitude a simple function (say linear) of the thoraxic position introduces new problems. Some positions are more likely to occur than others, and will probably repeat before the less likely positions occur the first time. This wastes time whatever is done with the redundant data obtained because of the repetitions (the redundant data can be discarded, averaged with the previous data from the same amplitude, etc.). Since the time to repeat and the breathing frequency are not synchronized some breathing cycle positions will occur a second or a third time before others have occured once. This happens because the breathing cycle position is "random" relative to the occurence of the encoding pulses and also because during the breathing cycles there are sections with relatively slow motion and others with relatively fast motion. The position axis values that are traversed during the part of the cycle where the motion is slow are more likely to be detected in a random sampling arrangement than the position axis values traversed where the motion is fast; partially because the slower motion part of the breathing cycle extends over a longer time period.

Another solution tried has been the use of the integral of the temporal probability function of the thoraxic position as the mapping function for position vs. encoding pulse amplitude. This creates a flat, nearly constant probability function for the encoding amplitudes. However, as the thoraxic position is a function of the breathing process and is independant of TR, the position is random relative to the pulse train number. The statistical nature of the sampling will, therefore, cause some positions to repeat numerous times before other positions occur even once. Thus, this solution is also not sufficiently efficient.

In one particular prior art method used to speed up the process of activating all of the required encoding pulses, the encoding pulse amplitudes per pulse repetition are selected using "bins" instead of varying the amplitude of each ensuing encoding pulse as a direct function of the thoraxic or breathing cycle. Each bin is defined by a range of respiratory cycle positions. A range of encoding pulse amplitudes is assigned to each bin. Each received breathing cycle position then determines a bin and the next encoding pulse amplitude is selected from the determined bin.

There may be different methods of selecting the encoding pulse amplitude once the bin is selected. For example, the central amplitude allocated to the bin may be the amplitude of first choice when the breathing cycle position first indicates a particular bin. At the second indication of the particular bin, the first amplitude greater than the central amplitude is selected. The third indication of the particular bin selects the encoding pulse amplitude immediately less than the central amplitude. This process continues until all of the encoding pulse amplitudes assigned to each of the particular bins are used.

The bin methods also increase the data acquisition time. For example, if each bin includes only one encoding amplitude; then if a breathing cycle position is sampled which has already been sampled, (double sampling) the immediate reaction is to skip it. A few sequences of the data could perhaps be skipped without serious loss. However, as more and more encoding amplitudes are used it becomes increasingly more probable that the next sampled position of the breathing cycle will be a double sampling. The probability of sampling a previously unsampled breathing position decreases with time both because less sample positions are left and because the more probable positions are usually sampled earlier. The last few encoding amplitudes may therefore require a large number of "aborted" samplings and a very long marginal time to obtain. Larger bins alleviate the problem of cancellation but fail to eliminate the problem of motion artifacts.

Use of different, more complicated binning methods may indeed decrease the acquisition time but only partially solve the problem of the artifacts. Consider that the sampling of the breathing cycle position is random relative to the encoding pulse time, therefore, statistically one of the bins will always be used up first, because this bin has a higher probability of utilization and therefore will be double sampled with a consequent waste of time.

Still another problem with the binning solutions is that such solutions assume a constant unchanging breathing cycle. In practice breathing cycles tend to vary in amplitude, time and shape. For example, the amplitude may decrease, thereby eliminating the sampling of certain positions and consequently creating the possibility of corresponding bins not being used entirely or only being partially used. Attempted solutions to the problems raised by varying breathing cycles include limiting the transformation function to a region smaller than that indicated by the breathing amplitude as determined preliminarily and using bins of equal probability rather than bins of equal intervals.

Limiting the transformation function to a region smaller than the breathing cycle tends to erase part of the breathing cycle. Using bins of equal probability suffers because breathing cycle position probabilities also change with variations in the breathing cycles and the bin sizes are therefore no longer are optimal.

BRIEF DESCRIPTION OF THE INVENTION

Accordingly, it is an object of this present invention to provide apparatus and processes for reducing breathing artifacts obtained during MRI data acquisition used for diagnostic purposes. More particularly, a method of reducing motion artifacts in magnetic resonance imaging is provided using detected respiration cycle parameters to determine the next encoding cycle amplitude to be used in the image data acquisition scan sequences, said method comprising the steps of:

determining the amplitude and time parameters of the respiration cycle of a subject to be scanned, dividing the respiration cycle amplitude into intervals, assigning at least one preferred phase encoding pulse amplitude to each of the intervals according to the amplitude of the respiration cycle of the subject being scanned, selecting encoding pulses with the encoding pulse amplitudes being the preferred amplitude assigned to the detected interval at the time of encoding pulse selection, determining whether or not said selected encoding pulse amplitude has been used, and selecting the closest non-used amplitude to replace the used preferred amplitude.

A feature of the present invention limits the substitution of the closest unused amplitude for the preferred amplitude to an amplitude within X % of the preferred amplitude, whereby certain measurements are discarded, where the percentage is a function of the regularity of the patients breathing and the doctor can choose the percentage.

BRIEF DESCRIPTION OF THE DRAWINGS

The above named and other features and objects of the present invention believed to be novel are set forth with particularity in the appended claims; while the invention itself will be best understood along with the advantage thereof by referring to the following description, taken in conjunction with the accompanying drawing, in which:

GENERAL DESCRIPTION

Figure 1:
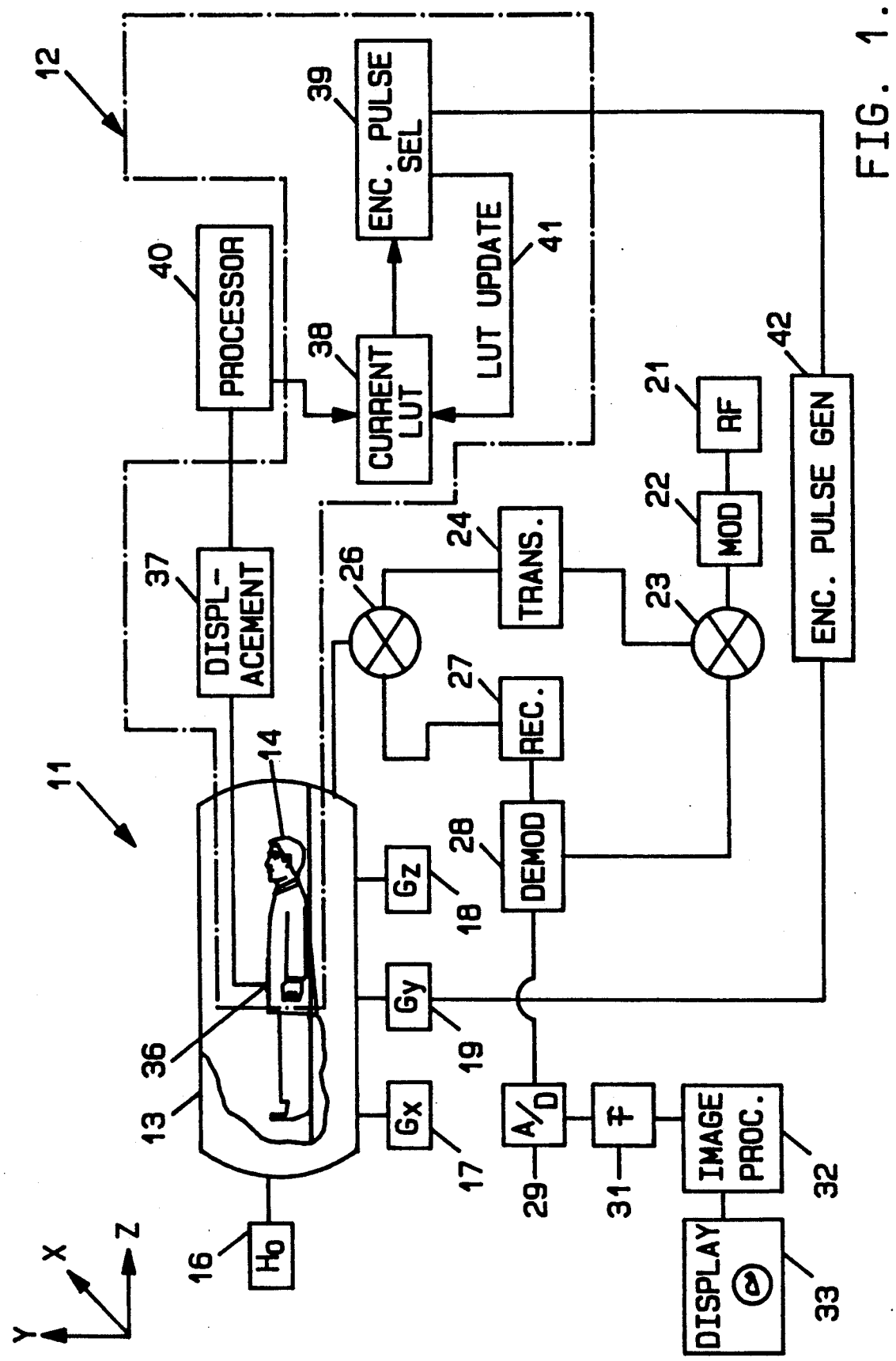
FIG. 1 depicts in block diagram form the inventive system.

A system 11 is shown in FIG. 1 for use in acquiring MRI data. The system 11 includes an arrangement for minimizing or reducing motion artifacts generally indicated at 12. The general system 11 includes a large magnet 13 for creating a large static magnetic field into which a patient 14 is placed. To obtain image data the large static magnetic field is generated using the magnet in conjuction with a large magnetic field generator 16 indicated at block HO. The large static magnetic field causes certain nucleii or "spins" to align with the field. Orthogonal gradients are used to locate the source of what is referred to as free induction decay FID signals received from the patient. The term free induction decay signals as used herein also includes echo signals. The gradients are generated by the X gradient generator 17, the Z gradient generator 18 and the Y gradient generator 19.

The large static magnetic field, according to the explaination given herein, is in the Z direction. However, the direction of the large static field and the other gradient fields can be changed to suit the user and still be within the scope of this invention.

As is well known, to obtain FID signals it is necessary to "tip" the spins from the normal position aligned with the large static magnetic field in the Z direction to a position having at least a projection in the XY plane. Radio frequency (RF) pulses having a desired frequency (known as the Larmor frequency) are used to tip the spins. The RF pulses are transmitted through RF probes or coils (not shown) used in the system. An RF generator 21 is used to generate the radio frequency pulse which may be modulated by modulator 22 and switched by switch 23 to a transmitter 24 for connection to the RF coil.

The transmission of the pulse is shown as going through a switch 26 to enable using a single coil for both transmitting and receiving, for example.

In the normal mode of operation the Z gradient is used as a plane selecting gradient; that is the RF pulse is applied during the application of the Z gradient. The Z gradient or plane selecting gradient may or may not be applied within the scope of the present invention.

The signals which are received after the RF pulse has been terminated are detected by either the same coils used for transmitting or by separate receiving coils. In either case, the coil is attached to receiver 27 through the switch 26. The received signal is connected to a demodulator 28. The demodulator also receives a modulator generated signal from switch 23. The demodulated received signals are converted from analog to digital signals in an analog to digital convertor 29. The digital signals from the analog to digital convertor 29 are then operated on and transferred from the frequency domain to the time domain by the Fourier operator 31. The time domain signals are processed in an image processor 32 to provide an image on display unit 33.

The X gradient is used as a view gradient; that is in a preferred embodiment, an X-gradient is applied during the receipt of echo signals obtained in response to the application of any of the well known echo providing scan sequences. That is, the scan sequence can either be designed to obtain a Hahn echo or a gradient echo or combinations of Hahn and gradient echoes.

The image processor processes the received signals so that a pixel value is provided for each pixel in the image. For example, in the usual case, the image is made up of 256 by 256 pixels arranged in X columns and Y rows. The pixel values are obtained after the operation of the Fourier transform on the echo signals received. The transformed data is comprised of wave number related amplitudes where the pertinent X-wave numbers are generated as a function of time over the X gradient and the Y wave numbers are generated by integrating the Y gradient over time. The Y gradients are proportional to the "encoding pulse" amplitudes.

To minimize artifacts due to motion between rows, the values of the encoding pulse amplitude used are selected by the vertical position of the patient's thorax, for example. This type of artifact correction minimizes the most problematical of the motion artifacts which are the artifacts in the time or phase encoding direction. These artifacts cause the most problems because there is a larger time period between changing the vertical (Y) wave numbers i.e. the encoding amplitudes compared to changing the horizontal (X) wave numbers. In other words, the Y encoding wave numbers are changed less frequently then the X encoding wave numbers which are usually changed at each sampling within each echo signal received. The Y encoding gradient, consequently the Y wave number changes once per repetition of the scan, i.e., once per time to repeat (TR).

Means including sensor 36 are provided for measuring the vertical positioning of the patient's thorax; i.e. displacement versus time caused by the patient's breathing. After a preliminary or learning period, the displacement characteristic is transformed into a preferred look-up table: that is, each displacement position is assigned a preferred encoding gradient pulse amplitude. Preferably the transformation of the displacement characteristic is accomplished by the system processor, a portion of which is shown at 40, connected between the displacement encoding device 37 and a current preferred look-up table 38. A special computer could also perform this function of the system processor. While it is not shown in the drawing for purposes of simplification, the processor is connected to all units requiring control signals.

The total displacement of the patient's thorax due to breathing is preferably divided into N displacement values where N is a number of bits, for example, 256 displacement values. For each of the 256 displacement values, a preferred phase encoding pulse amplitude is assigned. Thus, there is one preferred phase encoding pulse amplitude per each displacement interval. The transducer 36 senses the displacement and outputs a voltage. The voltage is encoded in the displacement encoding device 37 to provide a displacement position ranging from 0 to 255 or from −128 to +128. For purposes of this description, 0 to 255 will be used; however, the displacement can just as well be from −128 to +128.

Each measured displacement is fed into the current preferred look-up table 38. The current preferred look-up table has a preferred phase encoding pulse amplitude for each of the 256 displacement positions. Thus, each displacement position from 0 to 255 provides an encoding pulse amplitude which can be designated by the numbers 0 to 255. When the phase encoding pulse is selected, the selection is transferred to the phase encoding pulse selection circuit 39. The selection circuit 39 feeds back the selected encoding amplitude over conductors 41 to modify the look-up table by removing the selected encoding pulse from the look-up table and replacing it with the selected encoding pulse amplitude plus one.

For example, where the displacement 64 was detected the look-up table selected phase encoding pulse 64. After the selection the look-up table for the same displacement 64 now indicates that the encoding pulse to be selected will be 65. If 65 has also previously been selected, then the look-up table is modified and updated to show that the displacement amplitude 64 will select phase encoding pulse amplitude 63. This modification of look-up table is continuous and it occurs every time an encoding pulse amplitude is selected. In a preferred embodiment the replacement of the selected phase encoding pulse amplitude continues until phase encoding pulse amplitudes of up to plus or minus 50% away from the amplitude of the originally preferred phase encoding pulse are used before data is discarded. After that, the received signal for the displacement will be discarded.

Responsive to the operation of the phase encoding pulse amplitude selector, an encoding pulse generator 42 operates to supply the encoding pulse amplifier 19 with the phase encoding pulse of the required amplitude. This is a modification of the well known "ROPE" method previously referred to which causes the breathing motion to appear as a slowly changing function rather than a cyclical function.

In operation, the displacement measuring equipment is preliminarily operated to measure the normal total displacement of the patient's chest due to respiration. Based on the total respiration displacement a preferred encoding pulse amplitude is assigned in a current LUT to each of the total number of displacement positions. Once the current LUT has been determined the actual tests are run. At that time, a scan sequence is run to provide echo signals. Prior to the receipt of the echo when the phase encoding pulse is to be applied the displacement of the patient's thorax is measured. An encoding pulse having an amplitude as determined by the thorax displacement using the current look-up table is provided. The encoding pulse generator then generates a phase encoding gradient pulse having the preferred amplitude. Immediately, the current look-up table is updated so that a sequential phase encoding gradient pulse amplitude is generated responsive to the same thorax displacement. This process continues until 256 encoding pulses have been applied and sufficient data has been acquired to provide the image on display means 33.

Thus, in this version of the motion artifact reducer, the phase encoding gradient pulse amplitude Ai is always equal to the product of the presently read displacement Di divided by the total displacement Dt times the total encoding pulse amplitude At plus or minus n (where n is an integer equal to the number of times the same thorax displacement has been detected) minus 1. Mathematically:

$$Ai = \left[\left(\frac{Di \cdot At}{Dt}\right) \pm (n - 1)\right](G + K)$$

where:
G is a scaling factor; (to match the gradient scale to the breathing output);
K is a constant reflecting the offset between scales.

While the invention has been described with reference to particular embodiments, it should be understood that these embodiments are described by way of example only and not as limitations on the scope of the invention. Accordingly, it should be understood that within the scope of the appendant claims the invention may be practised other wise than as specifically described.

What is claimed is:

1. A method of reducing respiratory motion artifacts generated while acquiring magnetic resonance imaging (MRI) data of a subject, said method comprising the steps of:
    subjecting the subject to a large static magnetic field,
    determining a normal maximum amplitude of the subject's respiration cycle measuring from the subject's back to the subject's thorax,
    dividing the normal maximum amplitude of the respiration cycle into a number of respiration cycle intervals,
    assigning a preferred phase encoding gradient pulse amplitude to each of the intervals,
    using a multi-dimensional data acquisition scan sequence with one dimension determined by phase encoding gradient pulses to obtain signals from the subject for use in acquiring magnetic resonance images,
    determining the respiration cycle interval at a time for use of one of said phase encoding gradient pulses,
    selecting the assigned preferred phase encoding gradient pulse amplitude to be used according to the determined respiration cycle interval of the subject at the time for use of the one of said phase encoding gradient pulses,
    selecting another assigned preferred phase encoding gradient pulse, if the previously selected assigned preferred phase encoding gradient pulse has already been used, and said last named selecting step including acquiring data using a next sequential unused phase encoding gradient pulse in place of the previously selected assigned preferred phase encoding gradient pulse up to a next sequential unused phase encoding gradient pulse that has an amplitude that is different than the first selected assigned preferred phase encoding gradient pulse amplitude by X %.

2. The method of claim 1 wherein said multi-dimensional scan sequence is a two-dimensional scan sequence.

3. The method of claim 2 including the step of determining if the selected assigned preferred phase encoding gradient pulse amplitude has already been used, said step of determining whether the assigned preferred phase encoding gradient pulse amplitude has already been used being before the selecting step.

4. The method of claim 2 including the step of determining which phase encoding gradient pulse amplitudes are available prior to selecting the phase encoding pulse.

5. The method of claim 4 including the steps of storing phase encoding gradient pulse amplitudes,
    retrieving a phase encoding gradient pulse amplitude from storage responsive to said determined interval, and
    generating a phase encoding gradient pulse in accordance with the phase encoding gradient pulse amplitude retrieved.

6. The method of claim 5 including the step of preparing a look-up table for indicating a phase encoding gradient pulse amplitude to be used for generating the phase encoding gradient pulse responsive to said determined respiration cycle interval.

7. The method of claim 6 including the step of updating the look-up table each time a phase encoding gradient pulse amplitude assigned to an interval in said look-up table is used.

* * * * *